United States Patent [19]

Mohiuddin

[11] Patent Number: 4,610,677
[45] Date of Patent: Sep. 9, 1986

[54] EXTENDED FILM SEAL FOR OSTOMY APPLIANCE

[75] Inventor: Mahmood Mohiuddin, Lake Zurich, Ill.

[73] Assignee: Hollister Incorporated, Libertyville, Ill.

[21] Appl. No.: 779,628

[22] Filed: Sep. 24, 1985

[51] Int. Cl.⁴ ............................................. A61F 5/44
[52] U.S. Cl. .................................... 604/339; 604/341
[58] Field of Search ................ 604/256, 277, 332–345

[56] References Cited

U.S. PATENT DOCUMENTS 3,331,370 7/1967 Notley, Sr. .......................... 604/342
4,419,100 12/1983 Alexander ........................... 604/341

FOREIGN PATENT DOCUMENTS 0098718 1/1984 European Pat. Off. ............ 604/342
44571 3/1935 France ................................ 604/332

Primary Examiner—C. Fred Rosenbaum
Assistant Examiner—J. L. Kruter
Attorney, Agent, or Firm—Tilton, Fallon, Lungmus

[57] ABSTRACT

An ostomy appliance including a collection pouch and a faceplate, each equipped with a flexible plastic coupling ring for detachably joining the faceplate and pouch. One of the rings includes a neck portion that protrudes through the opening of the other ring when the two are coupled together. An annular web of thin, flexible, stretchable plastic material is secured to the backside of the receiving ring and sealingly engages the protruding end of the neck portion when the two rings are latched together.

24 Claims, 9 Drawing Figures

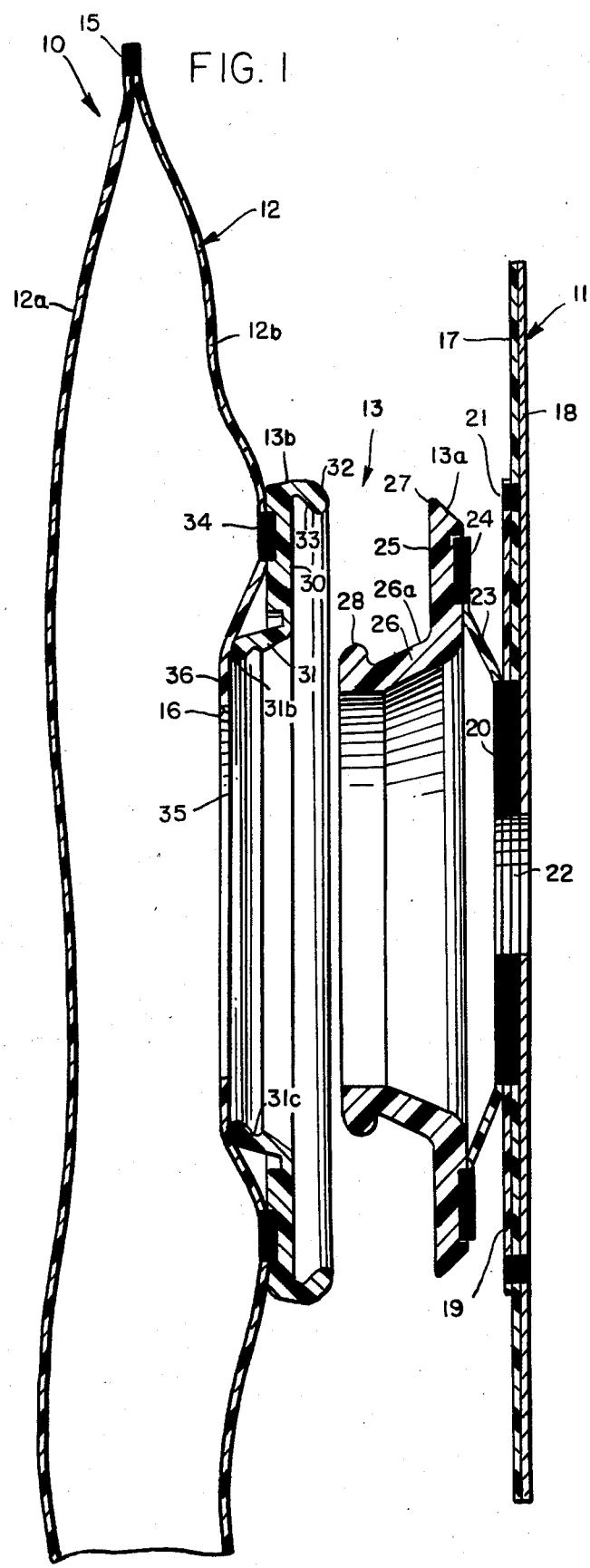
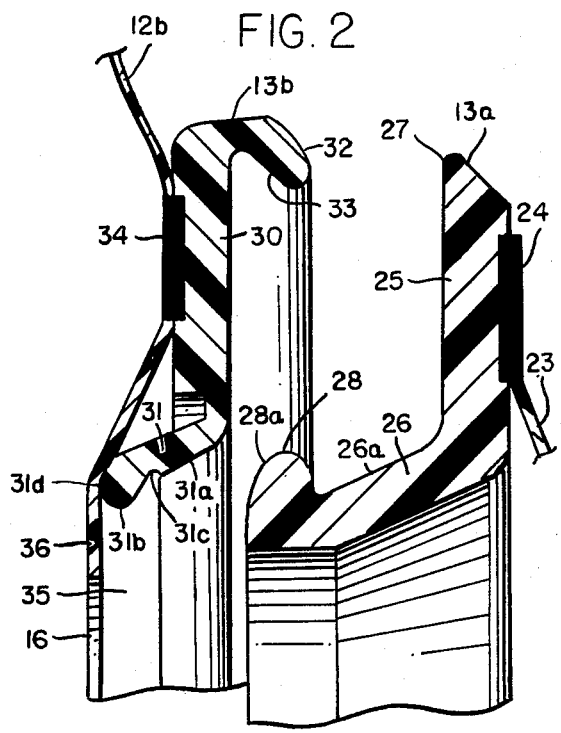
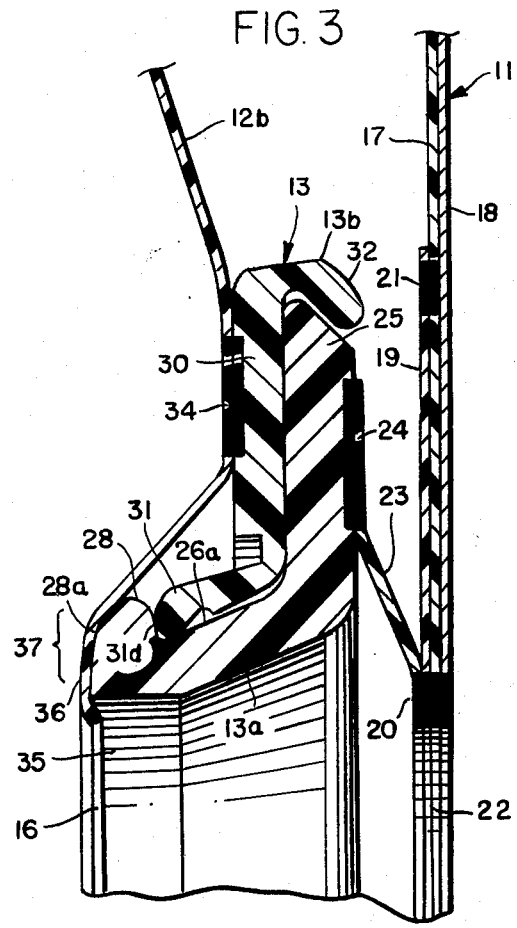

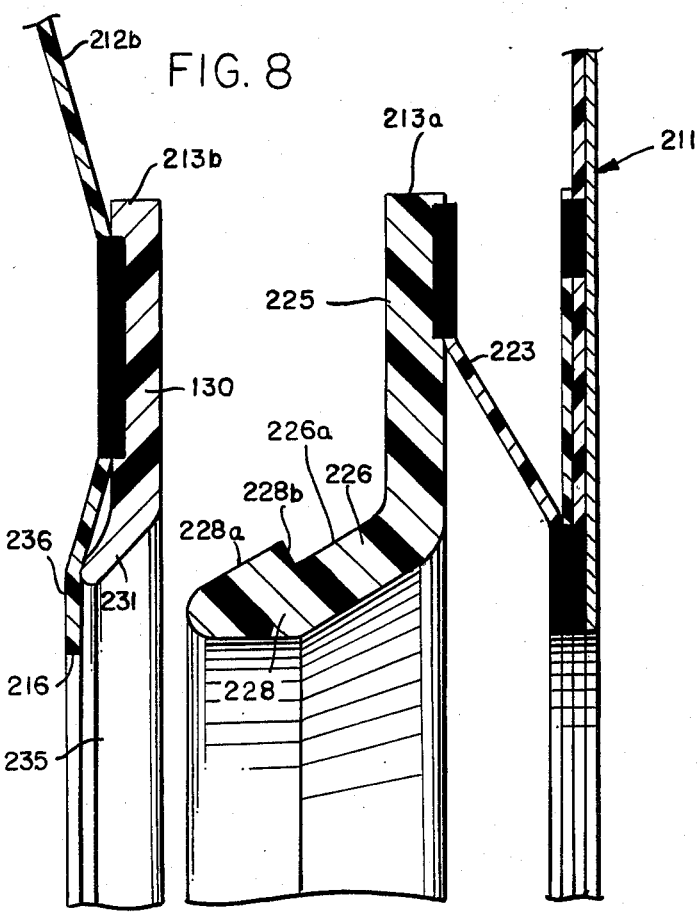
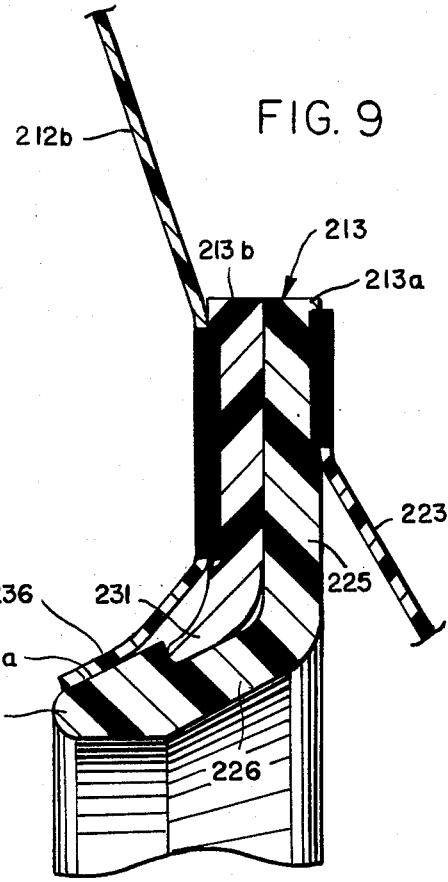

EXTENDED FILM SEAL FOR OSTOMY APPLIANCE

BACKGROUND

Ostomy appliances equipped with "two-piece couplings," as they are now commonly described, have been known for many years. For example, U.S. Pat. No. 3,528,420 discloses such an appliance having two deformable plastic rings, one of the rings 20 being secured to a faceplate 16 and the other ring 14 being attached to an ostomy pouch 10. A flange 26 on the inner ring is intended to provide an abutment for the outer ring to latch and seal the rings together until separation is desired.

Other types of two-piece couplings are known, as disclosed in U.S. Pat. Nos. 4,419,100, 4,170,231, 4,359,051, 3,948,256, and British Pat. No. 1,571,657. In all such constructions, latching and sealing functions are performed by the coupling rings themselves without the involvement or intervention of other elements or components. However, such sealing and latching functions may occur at different locations along the rings, as disclosed in co-pending co-owned application No. 611,423, filed May 17, 1984. In that application, one of the rings has an axially-extending frusto-conical neck portion and the other ring has a frusto-conical collar portion detachably receiving and sealingly engaging the neck portion. Primary latching is achieved in an annular zone spaced a substantial distance radially outwardly from the area of sealing engagement between the neck and collar portions, such latching action being provided by a shoulder extending about the outer periphery of one of the rings and a latching ring, defining a shoulder-receiving recess, extending about the outer periphery of the other ring.

SUMMARY OF THE INVENTION

This invention lies in part in the discovery that the sealing and latching functions of two-piece couplings may not only occur at different locations but that a thin flexible web secured to one of the rings may perform an important function in coacting with the other ring to form a fluid-tight seal. In a preferred embodiment, the web may be provided by, or constitute an extension of, the flexible film of the collection pouch itself. Reinforcement of the web may also be provided to insure effective fluid-tight sealing action with the annular rim of the neck. The result is a simple, inexpensive, and highly-effective seal between the parts.

The invention may be adapted for use with any two-piece coupling in which one coupling ring has a neck portion that is inserted into and protrudes through the opening of the other coupling ring when the two are latched together. The structure performing the latching function may take any of a variety of forms and is not critical to this invention except, of course, that some latching means must be provided. It is essential, however, that the neck portion of the first coupling ring not only extend through the opening of the second ring, but that such neck portion define a smooth annular surface that is disposed beyond the axial limits of the receiving (second) ring when the parts are latched together.

The protruding annular surface of the neck portion sealingly engages an annular web of film joined to the backside of the receiving ring—that is, the side of the receiving (second) ring facing away from the first ring. The web of flexible, stretchable film is tensioned by the protruding annular surface of the neck portion and coacts with that surface to produce a fluid-tight (including gas-tight) seal between the parts. Such seal may constitute the only seal or, preferably, may be a second (but not necessarily secondary) seal when the coupling rings are joined together.

In a preferred embodiment, the annular web of film is formed integrally with, or is sealed to, the film of the collection pouch. In such a construction, the coupling ring of the pouch therefore constitutes the receiving ring, and the faceplate coupling ring is the one provided with a neck portion that sealingly engages the web when the rings are latched together. Alternatively, the annular web may be joined to the faceplate ring which then serves as the receiving ring for receiving the web-engaging neck portion of the pouch ring when the parts are coupled. In any case, the flexible and stretchable web may be reinforced, or its cross section may be varied or contoured, to increase sealing effectiveness.

Other features, advantages, and objects of the invention will become apparent from the specification and drawings.

DRAWINGS

FIG. 1 is a vertical sectional view showing a faceplate and pouch with their respective coupling rings in detached condition.

FIG. 2 is an enlarged fragmentary sectional view of the parts in uncoupled condition.

FIG. 3 is an enlarged sectional view similar to FIG. 2 but showing the parts in coupled condition.

FIG. 8 is a fragmentary sectional view of a fifth embodiment showing the coupling rings in detached condition.

FIG. 9 is an enlarged sectional view similar to FIG. 8 but showing the rings in coupled condition.

DETAILED DESCRIPTION OF PREFERRED EMBODIMENTS

Figure 4:
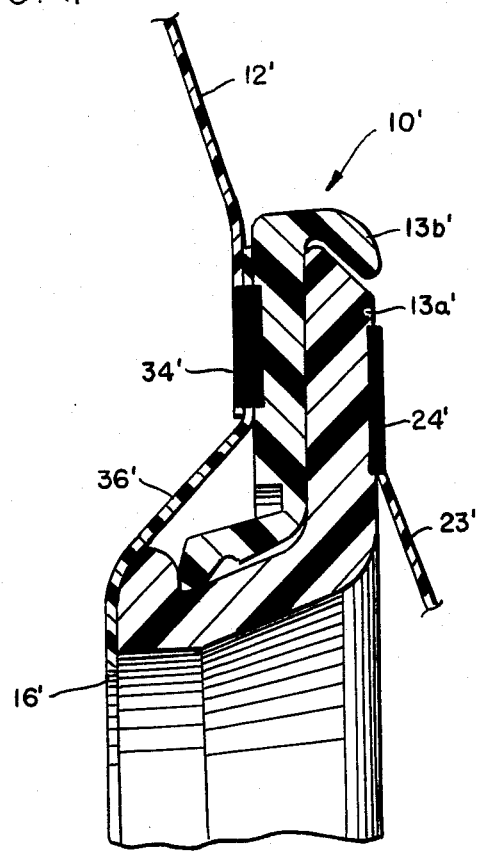
FIG. 4 illustrates a second embodiment of the invention in which the annular sealing web is not integral with the film of the pouch.

FIGS. 1-3 illustrate a preferred construction in which the coupling rings are essentially the same as disclosed in the aforementioned co-pending application No. 611,423. The ostomy appliance 10 includes a faceplate 11 and a bag or pouch 12. The two-piece coupling ring assembly 13 is provided for detachably coupling the faceplate and pouch, one element of the assembly being faceplate ring 13a and the other being pouch ring 13b.

Typically, pouch 12 is designed to be relatively flat and is composed of two sheets or walls 12a and 12b of flexible transparent material with odor-barrier properties, such sheets being heat sealed together along their outer margins as indicated at 15 in the drawings. One wall 12b, which may be regarded as the rear wall that would face the abdomen of a patient when the appliance is worn, is provided near its upper end with an opening 16.

Faceplate 11, in the particular form illustrated in the drawings, is constructed generally in accordance with the teachings of Pat. No. 4,213,458 and reference may be had to that patent for information on the details of construction. Faceplate 11 includes a highly flexible patch or panel 17 formed of gas-penetrable but water resistant microporous material. Various materials having such properties are known and may be used. The faceplate should be highly flexible so that it will conform readily to body contours and body movements, and be coated on its back or rear side with a medical-grade pressure-sensitive adhesive so that upon removal of backing sheet or sheets 18 the microporous adhesive-coated patch or panel 17 may be secured to the patient's skin in the peristomal region.

An attaching ring or collar 19 may be secured to the front face of the microporous patch 17 by heat sealing or by any other suitable means. In the illustrated embodiment, attaching ring 19 is heat sealed to the microporous patch along inner and outer concentric heat seal zones 20 and 21, respectively. The attaching ring reinforces the microporous patch 17 in the area about faceplate opening 22 and should be formed from a tough material capable of being securely joined to the patch. Thus, if the patch is formed of an ethyl vinyl acetate copolymer, the reinforcing attaching ring may be formed of a material of similar composition, although not necessarily microporous. The attaching ring must also be capable of being heat sealed or otherwise securely joined, either directly or indirectly, to ring 13a of the coupling ring assembly 13. In the construction depicted in the drawings, such connection is indirect to the extent that a web 23 of thin, flexible, and resilient thermoplastic material with odor barrier properties is interposed between faceplate ring 13a and attaching ring 19 of faceplate 11, as generally disclosed in co-owned Pat. No. 4,419,100. Specifically, the inner margin of annular web 23 is heat sealed at 20 to the attaching ring 19 of the faceplate 11 and its outer margin is heat sealed at 24 to faceplate coupling ring 13a. The web gives rise to a floating relationship between the faceplate ring 13a and faceplate 11, promoting conformity of the faceplate to a wearer's body without resistance from the coupling rings and, in general, allowing limited movement of the faceplate ring in generally axial directions with respect to the faceplate. Such limited movement allows a user to insert his (her) fingers between the ring 13a and faceplate 11 to facilitate attachment and detachment of the coupling rings without causing discomfort. The web 23 should be formed of a heat-sealable, tough, and durable material that is also capable of functioning as a fluid and odor barrier. Low density polyethylene coextruded with a coextensive layer or core of polyvinylidene chloride, known under the designation Saranex, from Dow Chemical Company, Midland, Mich., has been found suitable but other materials having similar properties are available and may be used.

Faceplate ring 13a has an annular body portion 25 and an integral tubular neck portion 26. It will be observed that the body portion 25 is planar and, specifically extends along a plane normal to the central axis of coupling ring 13a. At its outer limits, the planar body portion 25 provides an annular latching shoulder 27 that is shown to be continuous although, if desired, the latching shoulder may be discontinuous or interrupted along its circumference. The shoulder is rounded in longitudinal section to facilitate latching engagement with pouch ring 13b.

The neck portion 26 of ring 13a is generally frusto-conical in configuration and tapers axially and forwardly away from body portion 25. The smooth frusto-conical outer surface 26a of neck portion 26 is intended for sealing engagement with pouch ring 13b. At its front or distal end, neck portion 26 has an annular and radially-outwardly projecting rim 28 that has a rounded outer surface 28a when viewed in longitudinal section (FIGS. 2, 3).

The pouch coupling ring 13b is similarly provided with a body portion 30 that generally extends in a plane normal to the central axis of that ring. A generally frusto-conical collar portion 31 tapers axially from the inner margin of the body portion 30, the general direction of taper of collar portion 31 being the same as that of neck portion 26. The inner surface 31a of the collar portion is provided with an annular projection 31b adjacent the free end of the collar portion, such projection defining the smallest inside diameter of the collar portion for sealingly engaging the outer surface 26a of ring 13b. The smooth rounded projection 31b essentially makes a line seal with surface 26a and, to help insure sealing effectiveness, the inner surface of collar portion 31 may be recessed at 31c to provide greater definition for the annular projection 31b. At its distal or free end, collar portion 31 is provided with an axially-facing annular ridge 31d that normally abuts rim 28 when the parts are assembled as shown in FIG. 3.

Along its outer perimeter, body portion 30 merges with an annular latching rib 32 which projects inwardly and axially in a direction opposite from that of collar portion 31 and which, along with the remainder of body portion 30, defines an inwardly and rearwardly facing recess 33 for detachably receiving and retaining the shoulder 27 of faceplate ring 13a. The rib may be provided with rounded surfaces to facilitate latching engagement and disengagement of the two rings.

As shown most clearly in FIGS. 2 and 3, the pouch ring 13b is externally secured to the pouch along an annular sealing zone 34, preferably a heat-seal zone, that is concentric with and spaced radially outwardly from the opening 16 in pouch side wall 12b. It will be observed that the side wall opening 16 is substantially smaller than the opening 35 defined by the annular projection 31b of pouch ring 13b. As a result, an annular web of film 36 projects into the opening 35 of the pouch ring 13b.

Since the collar portion 31 of the pouch ring 13b projects axially towards the pouch beyond the annular heat seal zone 34 between the pouch and pouch ring, and since pouch wall 12b would assume a generally planar condition in an untensioned state, it is believed apparent that web 36 is in a state of tension even when the rings are uncoupled (FIG. 2). When the neck portion 26 of faceplate ring 13a is urged into the opening 35 of pouch ring 13b, the rounded rim 28 of the faceplate ring protrudes through pouch ring 13b and engages web 36 (FIG. 3). Specifically, the rounded surface 28a of rim 28 forceably and sealingly engages the web, displacing it forwardly into pouch 12. Since the web is in a state of tension, an effective fluid-tight (including gas-tight) seal occurs in the annular sealing zone designated by numeral 37 in FIG. 3.

A double seal is therefore produced by the disclosed construction, one seal occurring between ridge 31b of the pouch ring 13b and the radially-outward surface 26a of faceplate ring 13a, and the other occurring between rim 28 of the faceplate ring 13a and the extended film web 36. Increases in pressure within pouch 12 only force the extended film web into tighter sealing engagement with the rim 28 and, to the extent that the web exerts an axial force on rim 28, the force of sealing engagement between rim 28 and collar portion 31 is also increased.

In the embodiment of FIGS. 1–3, a major latching function is performed by latching rib 32 and latching shoulder 27. This outer latching zone is not a sealing zone for purposes of effectively preventing escape of fluids, and in fact a tight interfit between rib 32 and shoulder 27 should be avoided because it might interfere with completeness of sealing. The advantages of locating the latching zone radially outwardly from the sealing zone include the fact that the rings may be fabricated from softer and more pliable plastic materials without serious risk that deformation in use might result in unintentional disruption of the latching and sealing functions. While any of a variety of resilient and flexible plastic materials might be used for fabrication of the rings, low density polyethylene has been found particularly effective. Other tough, pliable materials that might be suitable are polyurethane, plasticized vinyl, and thermoplastic rubber.

Figure 5:
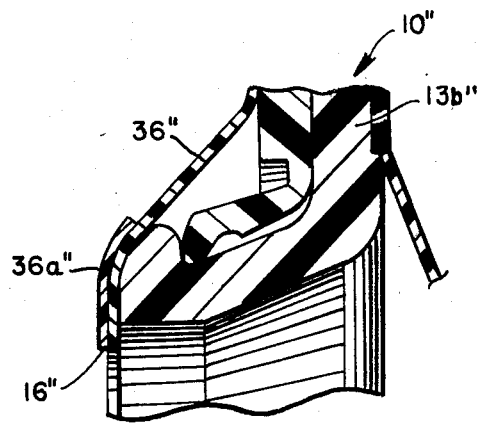
FIG. 5 is a fragmentary sectional view of a third embodiment of the invention.

The embodiments of FIGS. 4 and 5 are identical to the construction already described except for the annular sealing webs. In FIG. 4, web 36' is not formed integrally with the film of pouch 12' but is instead formed of a different material that is heat sealed at 34' (or otherwise suitably sealed) to coupling ring 13b'. Most advantageously, the same heat seal zone 34' may join both the annular web 36' and the wall of the pouch 12' to coupling ring 13b'.

As already described, the material of the annular sealing web should be both flexible and stretchable. The construction of FIG. 4 therefore permits the selection of a web material with properties better suited to the stretching and sealing functions than the material of the pouch 12'. More specifically, the web 36' may be formed of a material having greater elastomeric properties, less cold flow, better tensile strength, greater tear resistance, greater frictional properties, or different thickness, than the material of the pouch. In addition, the selection of a different material for web 36' may increase the options in the selection of material for pouch 12', since web 36' is interposed between the wall of the pouch and the coupling ring in heat seal zone 34'. Thus, a material may be selected for the wall of the pouch that is heat sealable to web 36' even though the same material is not directly or readily sealable to coupling ring 13b'.

In FIG. 5, web 36" may be integral with the wall of the pouch (as in FIGS. 1–3) or may be formed of a separate material (as in FIG. 4). A reinforcement 36a" is joined to web 36" at opening 16". Alternatively, the annular reinforcement 36a" may be integral with web 36", constituting an inner peripheral zone of increased thickness of the annular sealing web. By reinforcing or increasing the thickness of the web in the area of sealing contact with ring 13b'", it is believed apparent that the effectiveness of the seal may be enhanced while at the same time retaining optimum flexibility and stretchability of the remainder of the web.

Figure 7:
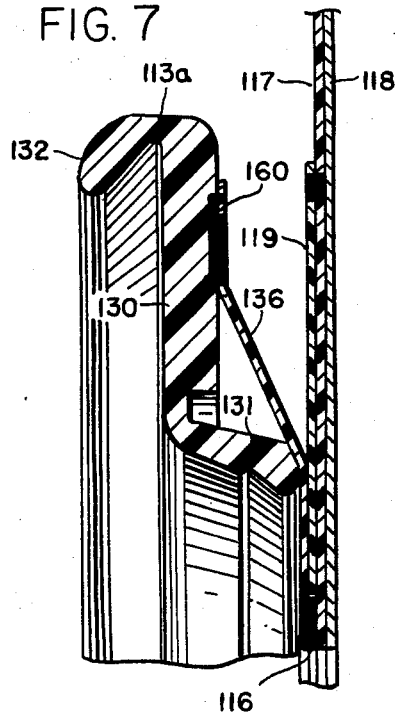
FIG. 7 illustrates the faceplate ring of FIG. 6 uncoupled from the pouch ring.
Figure 6:
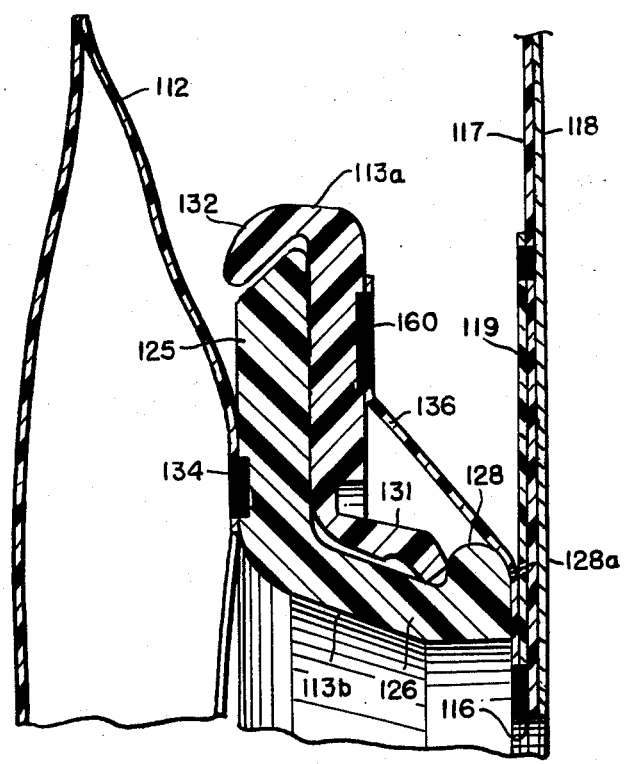
FIG. 6 is a vertical sectional view of a fourth embodiment in which the annular sealing web is joined to the faceplate ring, the two rings being shown in assembled condition.

FIGS. 6 and 7 illustrate how the relationship of parts might be reversed, with the annular sealing web 136 being secured to faceplate coupling ring 113a rather than to pouch coupling ring 113b. The pouch ring 113b has a planar body portion 125 that is heat sealed at 134 to pouch 112. It also includes a neck portion 126 and smooth annular rim 128 that protrude through the opening of faceplate ring 113a when the parts are assembled. The latching function is performed by collar portion 131 and latching rib 132 in essentially the same manner already described.

The annular sealing web 136 has its outer periphery sealed to the faceplate ring 113a by annular heat seal zone 160 or by any other suitable sealing means. The thin, flexible, and stretchable web 136 is in a state of tension even when the parts are uncoupled because the web, which would assume a planar configuration in an untensioned state, must extend inwardly about collar portion 131 (FIG. 7). The opening 116 defined by the annular web 136 is substantially smaller than the opening of collar portion 131. At its inner limits, the web is sealed to an attaching ring 119 which is in turn joined to adhesive-coated patch 117, the latter having its adhesive surface covered by release sheets 118.

When the coupling rings are latched together, the smooth rounded surface 128a of annular rim 128 of neck portion 126 sealingly engages web 136 as shown in FIG. 6. As already described, the web may be formed of any material having the desired properties of flexibility, stretchability, and durability. It is to be understood that reinforcement of web 136, as described in connection with the embodiment of FIG. 5, may also be provided.

It is believed apparent that the latching/sealing interconnection between the coupling rings of all of the embodiments so far described may be varied considerably while at the same time retaining an effective fluid-tight seal between an annular web and the protruding neck portion of the inserted coupling ring. For example, only a single latching zone may be provided between the two coupling rings, and the web may engage only an outwardly-facing surface portion of the rim of the inserted ring, as shown in the modified construction represented in FIGS. 8 and 9.

The coupling ring assembly 213 includes a faceplate ring 213a and a pouch ring 213b. The faceplate ring is connected to a faceplate 211 by means of a flexible web 223, both of which may be identical to faceplate 11 and web 23 of the embodiment of FIGS. 1–3. It is to be understood that while the inclusion of webs 223 and 23 in such embodiments has important advantages for the user, such webs 223 and 23 may be omitted, if desired, and faceplate rings 213a and 13a may be joined directly by heat sealing or otherwise to their respective faceplates.

Like faceplate ring 13a, the modified faceplate ring 213a includes a body portion 225 and a neck portion 226, the neck portion terminating in an enlarged annular rim 228. The rim is provided with a surface 228a which makes sealing engagement with the extended film web 236 of pouch wall 212b when the parts are coupled together as shown in FIG. 9.

The pouch ring 213b has a body portion 230 and a collar portion 231, the latter defining an opening 235 which is substantially larger than the opening 216 of web 236. When the rings are coupled together, the end of collar portion 231 abuts the rearwardly-facing surface or shoulder 228b of the annular rim 228, thereby latching the two rings together. Some outward flexure of collar 231 must occur in order to accommodate the neck portion 226 of the faceplate ring 213a with the result that a tight sealing engagement occurs between the inwardly-facing surface of collar portion 231 and the outwardly-facing surface 226a of neck portion 226 (FIG. 9).

Of particular importance is the fluid-tight seal produced by the radially outward displacement of web extension 236, the tensioning of that web, and its forceful sealing engagement against surface 228a of rim 228.

In function and operation, the embodiment of FIGS. 8 and 9 is similar to the previous embodiments except that only a single latching zone is provided and the seal between the extended web and that portion of the faceplate ring that protrudes into the pouch takes place along a radially-outwardly facing surface 228a rather than along a forwardly-facing surface. Additionally, in the modified construction the inner limits of annular web portion 236 do not project into the opening of faceplate ring 213 when the rings are coupled together (FIG. 9).

While in the foregoing, embodiments of the invention have been disclosed in considerable detail for purposes of illustration, it will be understood by those skilled in the art that many of these details may be varied without departing from the spirit and scope of the invention.

I claim:

1. An ostomy appliance comprising a collection pouch formed of flexible plastic film and including a side wall having an opening therethrough; a pouch coupling ring having an opening and being externally secured to said pouch about said side wall opening; a faceplate to be adhesively and peristomally secured to a patient; a faceplate coupling ring having an opening and being mounted upon said faceplate; means provided by said rings for detachably latching the same together; one of said rings having a neck portion with a smooth continuous annular rim projecting through the opening of the other of said rings when said rings are latched together; and an annular web secured to a surface of said other ring facing away from said one ring and defining an opening concentric with and smaller than the opening of said other ring; said annular web being formed of flexible, stretchable plastic material and sealingly engaging said annular rim of said neck when said rings are latched together.

2. The ostomy appliance of claim 1 in which said one ring is secured to said faceplate and said other ring is secured to said pouch.

3. The ostomy appliance of claim 1 in which said one ring is secured to said pouch and said other ring is secured to said faceplate.

4. The ostomy appliance of claim 2 in which said annular web is is integral with the film of said pouch.

5. The ostomy appliance of claim 1 in which said web has portions of different thickness.

6. The ostomy appliance of claim 5 in which said web has a reinforced inner periphery of increased thickness.

7. The ostomy appliance of claim 3 in which said annular web is secured about the opening thereof to said faceplate and has its outer periphery secured to said faceplate coupling ring.

8. An ostomy appliance comprising a collection pouch formed of flexible plastic material having a side wall opening; a pouch ring externally secured to said pouch about said opening; an apertured faceplate to be adhesively and peristomally secured to a patient; a faceplate ring mounted upon said faceplate and having a neck portion insertable into and latchable with said pouch ring; said neck portion terminating in an annular rim projecting into said pouch beyond said pouch ring when said rings are latched together; and an annular web permanently secured to a surface of said pouch ring facing said pouch and defining an opening smaller than and concentric with the opening of said pouch ring; said annular web being formed of flexible, stretchable plastic material and sealingly engaging said rim of said faceplate ring when said rings are latched together.

9. The ostomy appliance of claim 8 in which said rim provides a smooth rounded surface sealingly engagable with said annular web.

10. The ostomy appliance of claim 8 in which said rings are formed of flexible and resilient plastic material.

11. The ostomy appliance of claim 10 in which said pouch ring includes an annular collar portion normally sloping axially and radially inwardly into said pouch; said neck portion of said faceplate ring having an external latching shoulder engagable with said collar portion for releasably latching said rings together.

12. The ostomy appliance of claim 8 in which said annular web is formed integrally with the flexible plastic material of said pouch.

13. The ostomy appliance of claim 8 in which said annular web has an outer periphery sealed to both said pouch ring and said plastic material of said pouch.

14. The ostomy appliance of claim 8 in which said annular web has an annular portion about the opening thereof of increased wall thickness.

15. The ostomy appliance of claim 14 in which said increased wall thickness is provided by an annular reinforcement secured to said web.

16. An ostomy appliance comprising a collection pouch formed of flexible plastic material having a side wall opening; a pouch ring externally secured to said pouch about said opening and having an annular neck portion projecting away from said opening and terminating in an annular rim; a faceplate ring secured to said faceplate by an annular web of flexible, stretchable plastic material having its outer periphery sealed to said faceplate ring and its inner periphery sealed to said faceplate; said neck portion of said pouch ring being insertable into and latchable with said faceplate ring; said annular rim projecting through the opening of said faceplate ring and sealingly engaging said stretchable annular web when said rings are latched together.

17. The ostomy appliance of claim 16 in which said rim provides a smooth rounded surface sealingly engagable with said annular web.

18. The ostomy appliance of claim 16 in which said rings are formed of flexible and resilient plastic material.

19. The ostomy appliance of claim 18 in which said faceplate ring includes an annular collar portion normally sloping axially and radially towards said faceplate; said neck portion of said pouch ring having an external latching shoulder engagable with said collar portion for releasably latching said rings together.

20. An ostomy pouch formed of flexible plastic film and including a side wall having an opening therethrough; a pouch coupling ring having an opening and being externally secured to said pouch about said side wall opening; said pouch coupling ring having means for latching engagement with a faceplate coupling ring insertable into the opening of said pouch coupling ring; and an annular web of flexible and stretchable plastic film secured to said pouch coupling ring along the side of said ring facing said pouch and defining an opening concentric with and substantially smaller than the opening of said pouch coupling ring; said annular web being disposed for sealing engagement with a faceplate coupling ring insertable into said pouch coupling ring.

21. The ostomy pouch of claim 20 in which said annular web of plastic film is formed integrally with the plastic film of said pouch.

22. The ostomy pouch of claim 20 in which said annular web and said film of said pouch are each secured to said pouch coupling ring.

23. The ostomy pouch of claim 20 in which said annular web of flexible and stretchable film includes a reinforced portion of increased thickness immediately about the opening therethrough.

24. An ostomy faceplate having an aperture and having means for adhesively and peristomally securing said faceplate to a patient; faceplate coupling ring means having an opening for receiving and latching with the annular neck portion of a pouch coupling ring; and annular web means of flexible and stretchable plastic film disposed between said faceplate and said faceplate coupling ring means; said web means having an outer peripheral portion secured to said faceplate coupling ring means and an inner peripheral portion secured to said faceplate, and defining an opening substantially smaller than the opening of said faceplate coupling ring means; whereby, said flexible and stetchable annular web means is positioned for sealing engagement by the neck portion of a pouch coupling ring means inserted through the opening of said faceplate coupling ring means for latching therewith.

* * * * *